United States Patent
Becker et al.

(10) Patent No.: US 6,946,570 B2
(45) Date of Patent: *Sep. 20, 2005

(54) ESTER SYNTHESIS

(75) Inventors: Stanley John Becker, Addlestone (GB); Geoffrey Bryne, Bishopston (GB); Simon Frederick Thomas Froom, Snaith (GB); Stephen Robert Hodge, Beverley (GB)

(73) Assignee: BP Chemicals Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/785,190

(22) Filed: Feb. 25, 2004

(65) Prior Publication Data

US 2004/0167353 A1 Aug. 26, 2004

Related U.S. Application Data

(63) Continuation of application No. 09/215,299, filed on Dec. 18, 1998, now abandoned.

(30) Foreign Application Priority Data

Dec. 23, 1997 (GB) ............................................. 9727032
Aug. 12, 1998 (GB) ............................................. 9817572

(51) Int. Cl.$^7$ ......................... C07C 67/02; C07C 67/00; B01J 10/00
(52) U.S. Cl. ....................... 560/241; 560/247; 560/248; 422/129; 422/196; 422/197
(58) Field of Search ................................ 560/247, 241, 560/248, 560; 422/129, 196, 197

(56) References Cited

U.S. PATENT DOCUMENTS

| | | | |
|---|---|---|---|
| 3,644,497 A | 2/1972 | Mesich | 560/247 |
| 4,205,182 A | 5/1980 | Izumi et al. | 560/247 |
| 4,405,808 A | 9/1983 | Nakajima et al. | 560/247 |
| 4,927,954 A | 5/1990 | Knopf et al. | 558/441 |
| 5,241,106 A | 8/1993 | Inoue et al. | 560/247 |
| 6,794,535 B2 * | 9/2004 | Froom et al. | 560/247 |

FOREIGN PATENT DOCUMENTS

| | | |
|---|---|---|
| EP | 0 538 826 A2 | 4/1993 |
| EP | 0 562 139 A1 | 9/1993 |
| EP | 0 562 139 B1 | 9/1993 |
| EP | 0 757 027 A1 | 2/1997 |
| JP | HEI 7-17907 * | 1/1995 |
| JP | A 2674699 | 1/1995 |

* cited by examiner

Primary Examiner—Cecilia J. Tsang
Assistant Examiner—Taylor Victor Oh
(74) Attorney, Agent, or Firm—Nixon & Vanderhye

(57) ABSTRACT

This invention relates to a process for the production of lower aliphatic esters by reacting a lower olefin with a saturated lower aliphatic mono-carboxylic acid in the vapor phase in the presence of a heteropolyacid catalyst in a plurality of reactors set up in series such that the reactant gases exiting from a first reactor are fed as the feed gas to a second reactor and those exiting from the second reactor are fed as the feed gas to a third reactor and so on for the subsequent reactors. An aliquot of the reactant monocarboxylic acid is introduced into the feed gas to the second and subsequent reactors so as to maintain the olefin to monocarboxylic acid ratio in the feed gas to each of the second and subsequent reactors within a pre-determined range.

24 Claims, No Drawings

ESTER SYNTHESIS

This application is a continuation of application Ser. No. 09/215,299, filed Dec. 18, 1998 now abandoned, the entire content of which is hereby incorporated by reference in this application.

The present invention relates to a process for the synthesis of esters by reacting an olefin with a lower carboxylic acid in the presence of an acidic catalyst.

It is well known that olefins can be reacted with lower aliphatic carboxylic acids to form the corresponding esters. One such method is described in GB-A-1259390 in which an ethylenically unsaturated compound is contacted with a liquid medium comprising a carboxylic acid and a free heteropolyacid of molybdenum or tungsten. This process is a homogeneous process in which the heteropolyacid catalyst is unsupported. A further process for producing esters is described in JP-A-05294894 in which a lower fatty acid is esterified with a lower olefin to form a lower fatty acid ester. In this document, the reaction is carried out in the gaseous phase in the presence of a catalyst consisting of at least one heteropolyacid salt of a metal eg Li, Cu, Mg or K, being supported on a carrier. The heteropolyacid used is phosphotungstic acid and the carrier described is silica.

It has also been known that the addition reaction can be carried out in a plurality of reactors set up in series which reactors may be interspersed with an intermediate cooling stage because the reaction is exothermic and as the reaction mixture progresses through a series of such reactors the temperature could steadily rise and exceed the desired range thereby adversely affecting the reaction.

It has now been found that the process efficiency can be improved significantly by injecting further aliquots of acid to the reaction mixture.

Accordingly, the present invention is a process for the production of lower aliphatic esters said process comprising reacting in an addition reaction a lower olefin with a saturated lower aliphatic mono-carboxylic acid in the vapour phase in the presence of a heteropolyacid catalyst characterised in that the reaction is carried out in a plurality of reactors set up in series such that the gases comprising the unreacted gases and products exiting from a first reactor are fed as the feed gas to a second reactor and those exiting from the second reactor are fed as feed gas to the third reactor and so on for the subsequent reactors, and an aliquot of the reactant monocarboxylic acid is introduced into the feed gas to each of the second and subsequent reactors so as to maintain the olefin to monocarboxylic acid ratio in the feed gas to each of the second and subsequent reactors within a pre-determined range.

In the addition reaction, the olefin reactant used is suitably ethylene, propylene or mixtures thereof. Where a mixture of olefins is used, the resultant product will inevitably be a mixture of esters. The source of the olefin reactant used may be a refinery product or a chemical grade olefin which invariably contains some alkanes admixed therewith.

The saturated, lower aliphatic mono-carboxylic acid reactant is suitably a C1–C4 carboxylic acid and is preferably acetic acid.

The reaction mixture suitably comprises a molar excess of the olefin reactant with respect to the aliphatic mono-carboxylic acid reactant. Thus, the mole ratio of olefin to the lower monocarboxylic acid in the reactant gases fed to the first reactor is suitably in the range from 1:1 to 18:1, preferably from 10:1 to 14:1. During the reaction, when the reactant gases come into contact with the heteropolyacid in a catalyst bed, at lease some of the acid is used up to form the ester in an exothermic reaction and the mole ratio of olefin to monocarboxylic acid increases considerably from a starting ratio of 12:1 to about 30:1 in the exit gases from the final reactor. Where the reaction is carried out in a plurality of reactors set up in series, the exit gases comprising the unreacted materials and the ester product from the addition reaction from the first reactor are fed as the feed gas to the second reactor and the exit gases from the second reactor are fed as the feed gas to the third reactor and so on for subsequent reactors. When using such a series of reactors, the olefin to monocarboxylic acid mole ratio in the feed gas to each of the second and subsequent reactors is seriously depleted due to the acid being used up in the formation of the ester. This mole ratio of olefin to monocarboxylic acid is brought to the desired range by injecting further aliquots of the monocarboxylic acid to the feed gas prior to its entry into each of the second and subsequent reactors. In the case of the manufacture of ethyl acetate from ethylene and acetic acid, this range of mole ratios of ethylene to acetic acid in the reactant gases fed to the first reactor is suitably in the range from 1:1 to 18:1, preferably from 10:1 to 14:1 and that of the feed gas to the second and subsequent reactors is suitably from 10:1 to 16:1. The addition of further aliquots of the monocarboxylic acid to the feed gas to the second and subsequent reactors should be sufficient to bring the mole ratio of the olefin to acid within this range of 10:1 to 16:1.

The plurality of reactors set up in series referred to above can each be disposed in an axial mode with the feed and product gases traversing a substantially axial path within each reactor from entering the top of the reactor until the product gases leave each reactor from the base thereof, the catalyst being positioned somewhere midway between the point of entry of the feed gas and the point of exit of the product gases. However, the reactors need not be set-up in a series where the flow-path of the reactant and product gases are in a substantially axial direction within each reactor. They could be set-up as a series of radial flow reactors. In such a radial flow set-up, the feed gases will enter at the top of a reactor, pass down the middle thereof and then outwards radially over the catalyst in said reactor. Briefly, each radial flow reactor in the series is of a substantially tubular shape which in a planar view has the appearance of a set of three substantially concentric tubes and wherein the feed gases enter from the top into the inner most tube and flow substantially radially outward into a middle annular tube housing the catalyst bed and then, after the addition reaction has taken place over the catalyst bed to generate a gaseous stream of product gases comprising ethyl acetate and the unreacted feed gases, said gaseous stream emerging from the annulus comprising the catalyst bed flows further radially into the outermost tube of said concentric tubular reactor to be fed as feed gas into a second such radial flow reactor; and similarly the product gases exiting from the second reactor are used as feed for the third reactor in series and so on. The reactant acid is introduced into the gaseous streams emergent from each of (a) the first reactor to maintain the desired reactant concentrations in said gaseous stream so as to enable said stream to be used as the feed gas for the second and (b) the second reactor which is fed as the feed gas to the third reactor and so on to each of the subsequent reactors along in the series. The process can thus be operated by setting up a series of such radial flow reactors. One of the features of the radial flow reactors is that the pressure drop across such a reactor is much less when compared with a series of reactors set-up to operate in a mode where the feed gases and the product gases traverse a substantially axial path within each reactor.

Moreover, the velocity of the reactant gases over the catalyst bed is also comparatively lower, thereby minimising risk of damage to the catalyst due to attrition. When using radial reactors, there is a possibility that the catalyst bed settles or contracts within the annulus in which the catalyst bed is located creating a void space above the settled catalyst bed through which space the reactant gases may pass without making the desired contact with the catalyst. The risk of this happening may be averted by storing eg a volume of catalyst behind a screen located above the actual bed so that as the catalyst bed itself settles or contracts, a further aliquot of the catalyst is released from behind the screen to fill the voided space above the catalyst thereby minimising loss of the desired contact with the catalyst.

The plurality of reactors need not be a discrete set of individual reactors. The process of the present invention should also work equally effectively if the reaction is carried out in one long reactor which has a plurality of catalyst beds set up in series and the acid is injected into the exit gases from the first bed to maintain the range of olefin to monocarboxylic acid within the predetermined range in the second and subsequent beds. In a typical addition reaction it is desirable to use about four reactors set up in series although this can be reduced or increased without adversely affecting the beneficial effect of the injection of the monocarboxylic acid to the feed gas to the second and subsequent catalyst beds or reactors.

The reactors used in this context are suitably run under adiabatic conditions. Due to the exothermic nature of the addition reaction, it may be necessary to cool the feed gases to the second and subsequent reactors so as to maintain the reaction temperature within the desired range. This cooling may be achieved, where necessary, either by inserting an intermediate cooling step between the each of the reactors and can be wholly or partially replaced by the injection of the acid into the feed gas to the second and subsequent reactors. The intermediate cooling step can also be used where a single long reactor which has a plurality of catalyst beds set up in series is used. In this latter case, the intermediate cooling step is used to cool the reactant gases entering the second and subsequent catalyst beds. Where a cooling step is used, this may be achieved eg by:

a. using one or more of heat exchanger tubes, or
b. injection of:
   i. an additional amount of the monocarboxylic acid reactant or
   ii. water or
   iii. a suitable solvent, eg an alkane, which is either inert to the reaction system or is a reactant or a (by)product in the process into the feed gases as described above.

Whichever set up of reactors is used, the process of the present invention can be improved further by the addition of water as a component of the reaction mixture. The water added to the reaction mixture is suitably present in the form of steam and is capable of generating a mixture of esters and alcohols in the process. It has been found that the presence of water in the reaction mixture in an amount of 1–10 mole %, preferably from 3 to 7 mole %, eg 5 to 6.5 mole %, based on the total moles of acetic acid, olefin and water, enhances the stability of the catalyst and thereby enhances the efficiency of the process. Furthermore, the presence of water also reduces the selectivity of the process to undesired by-products such as eg oligomers and other unknowns, excluding diethyl ether and ethanol. Water addition may also supplement the cooling of the feed gases to the second and subsequent reactors as described above.

Where the reactant acid or an admixture thereof with another component such as water is used as the reactant/ coolant liquid in the present process, this admixture may by sprayed upwards into the or each of the first three reactors in a four-reactor system from the base thereof. This ensures sufficient mixing of the reactant/coolant liquid with the reactor gases. By spraying upwards, around the centre of the reactor, the sprays are able to vaporise within the recirculating feed gases and the spray is then entrained into the bulk flow. This spray may be achieved using one or more spray nozzles capable of delivering a fine spray of droplets suitably having an average droplet dimension of less than 200 microns. Thus, to achieve the desired flow rate of the admixture, a set of five spray arms is suitably used with four to five nozzles on each arm which will provide a maximum flow rate. It is preferable to provide an additional spray arm with a plurality of nozzles to mitigate any problems with any of the nozzles on one of the other five spray arms. A typical nozzle that may be used is the commercially available Schlick nozzle (type 121) which has a 2.0 mm diameter. The nozzles are suitably arranged in such a way that the spray from each nozzle does not interfere with those from other adjacent nozzles and thus do not cause coalescence. It is thus preferable that the nozzles are spaced at least about 200 mm apart, preferably 400 mm apart. The nozzles are suitably arranged in grid form about 1 meter below the base of the catalyst bed in each reactor, preferably in the centre half-radius of the reactor. This method is particularly suitable for use in conjunction with a set of radial flow reactors.

It has further been found that dosing the reaction mixture with amounts of a di-ether such as eg diethyl ether, as a co-feed also reduces the formation of undesirable by-products. The amount of di-ether co-fed is suitably in the range from 0.1 to 6 mole %, preferably in the range from 0.1 to 3 mole % based on the total of olefin, the aliphatic carboxylic acid, water and diethyl ether. The di-ether co-fed may correspond to the by product di-ether from the reaction generated from the reactant olefin. Where a mixture of olefins is used, eg a mixture of ethylene and propylene, the di-ether may in turn be an unsymmetrical di-ether. The di-ether co-feed may thus be the by-product of the reaction which by-product is recycled to the reaction mixture.

Furthermore, ethanol by-product can also be recycled in order to minimise build-up of relatively impure by-product ethanol which may otherwise have to be processed further, if pure ethanol has to be recovered therefrom. Inevitably, if ethanol is recycled to the feed gases comprising acetic acid, there may be some esterification of the ethanol to ethyl acetate in the presence of the acidic catalyst used in the process.

The term "heteropolyacid" as used herein and throughout the specification in the context of the catalyst is meant to include the free acids. The heteropolyacids used to prepare the esterification catalysts of the present invention therefore include inter alia the free acids and co-ordination type partial acid salts thereof in which the anion is a complex, high molecular weight entity. Typically, the anion comprises 2–18 oxygen-linked polyvalent metal atoms, which are called peripheral atoms. These peripheral atoms surround one or more central atoms in a symmetrical manner. The peripheral atoms are usually one or more of molybdenum, tungsten, vanadium, niobium, tantalum and other metals. The central atoms are usually silicon or phosphorus but can comprise any one of a large variety of atoms from Groups I–VIII in the Periodic Table of elements. These include, for instance, cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters". The structures of some of the well known anions are named after the original researchers in this field and are known eg as Keggin, Wells-Dawson and Anderson-Evans-Perloff structures.

Heteropolyacids usually have a high molecular weight eg in the range from 700–8500 and include dimeric complexes. They have a relatively high solubility in polar solvents such as water or other oxygenated solvents, especially if they are free acids and in the case of several salts, and their solubility can be controlled by choosing the appropriate counter-ions. Specific examples of heteropolyacids that may be used as the catalysts in the present invention include:

| 12-tungstophosphoric acid | $H_3[PW_{12}O_{40}].xH_2O$ |
| 12-molybdophosphoric acid | $H_3[PMo_{12}O_{40}].xH_2O$ |
| 12-tungstosilicic acid | $H_4[SiW_{12}O_{40}].xH_2O$ |
| 12-molybdosilicic acid | $H_4[SiMo_{12}O_{40}].xH_2O$ |
| Cesium hydrogen tungstosilicate | $Cs_3H[SiW_{12}O_{40}].xH_2O$ |

The heteropolyacid catalyst whether used as a free acid or as a partial acid salt thereof is suitably supported, preferably on a siliceous support. The siliceous support is suitably in the form of granules, beads, agglomerates, globules, extrudates or pellets.

The siliceous support used can be derived from a synthetic silica especially fumed silica, which may be amorphous, non-porous, such as those produced by flame hydrolysis of $SiCl_4$. Specific examples of such siliceous supports include Support 350 made by pelletisation of AEROSIL® 200 (both ex Degussa). This pelletisation procedure is suitably carried out by the process described in U.S. Pat. No. 5,086,031 (see especially the Examples) and is incorporated herein by reference. Such a process of pelletisation or extrusion does not involve any steam treatment steps and the porosity of the support is derived from the interstices formed during the pelletisation or extrusion step of the non-porous silica The silica support is suitably in the form of pellets or beads or are globular in shape having an average particle diameter of 2 to 10 mm, preferably 4 to 6 mm. The siliceous support suitably has a pore volume in the range from 0.3–1.2 ml/g, preferably from 0.6–1.0 ml/g. The support suitably has a crush strength of at least 2 Kg force, suitably at least 5 Kg force, preferably at least 6 Kg and more preferably at least 7 Kg. The crush strengths quoted are based on average of that determined for each set of 50 beads/globules on a CHATTILLON tester which measures the minimum force necessary to crush a particle between parallel plates. The bulk density of the support is suitably at least 380 g/l, preferably at least 440 g/l.

The support suitably has an average pore radius (prior to use) of 10 to 500 Å preferably an average pore radius of 30 to 100 Å.

In order to achieve optimum performance, the siliceous support is suitably free of extraneous metals or elements which might adversely affect the catalytic activity of the system. The siliceous support suitably has at least 99% w/w purity, ie the impurities are less than 1% w/w, preferably less than 0.60% w/w and more preferably less than 0.30% w/w.

Other silica supports are the Grace 57 and 1371 grades of silica. In particular, Grace 57 grade silica has a bulk density of about 0.4 g/ml and a surface area in the range of 250–350 m²/g. Grace silica grade No. 1371 has an average bulk density of about 0.39 g/ml, a surface area of about 500–550 m²/g, an average pore volume of about 1.15 ml/g and an average particle size ranging from about 0.1–3.5 mm. These supports can be used as such or after crushing to an average particle size in the range from 0.5–2 mm and sieving before being used as the support for the heteropolyacid catalyst.

The impregnated support is suitably prepared by dissolving the heteropolyacid, which is preferably a tungstosilicic acid, in eg distilled water, and then adding the support to the aqueous solution so formed. The support is suitably left to soak in the acid solution for a duration of several hours, with periodic manual stirring, after which time it is suitably filtered using a Buchner funnel in order to remove any excess acid.

The wet catalyst thus formed is then suitably placed in an oven at elevated temperature for several hours to dry, after which time it is allowed to cool to ambient temperature in a desiccator. The catalyst can also be dried suitably by using a flow of heated gas such as eg nitrogen or air. The catalyst loading in g/liter was determined by deducting the weight of the support used from the weight of the catalyst on drying.

Alternatively, the support may be impregnated with the catalyst using the incipient wetness technique and dried by using a flow of heated gas such as eg nitrogen or air.

This supported catalyst (measured by weight) can then be used in the process of the present invention. The amount of heteropolyacid deposited/impregnated on the support for use in the addition reaction is suitably in the range from 10 to 60% by weight, preferably from 20 to 50% by weight, more preferably from 20–35% by weight (corresponding to a loading in the range of about 100–215 g/liter) based on the total weight of the heteropolyacid and the support.

The reaction is carried out in the vapour phase suitably above the dew point of the reactor contents comprising the reactant acid, any alcohol formed in situ, the product ester and water as stated above. Dew point is the temperature at which condensation of a vapour of a given sample in air takes place. The dew point of any vaporous sample will depend upon its composition. The supported heteropolyacid catalyst is suitably used as a fixed bed in each reactor which may be in the form of a packed column. The vapours of the reactant olefins and acids are passed over the catalyst suitably at a GHSV in the range from 100 to 5000 per hour, preferably from 300 to 2000 per hour.

The addition reaction is suitably carried out at a temperature in the range from 150–200° C. within which range the entry temperature of the reactant gases is suitably from 160–180° C. and the temperature of the exit gases from each reactor is suitably 170–200° C. The temperature of the catalyst is slowly ramped up as the catalyst deactivates, eg by increasing the temperature of the feed to the first reactor, thereby maintaining productivity. The reaction pressure is suitably at least 400 KPa, preferably from 500–3000 Kpa, more preferably about 1000 Kpa depending upon the relative mole ratios of olefin to acid reactant and the amount of water used.

The products of the reaction are recovered by eg fractional distillation. The esters produced, whether singly or as mixture of esters, may be hydrolysed to the corresponding alcohols or mixture of alcohols in relatively high yields and purity.

The process of the present invention has a number of advantages:

a. It gives rise to increase catalyst productivity. This increase has two advantages: (i) Less catalyst is used and hence the reactor used can be smaller and cheaper, and (ii) the amount of olefin recycled is reduced due to higher olefin conversion per pass thereby lowering the costs by use of smaller equipment, especially recycle compressors.

b. It gives better control of catalyst conditions due to operation of the reactor under relatively narrower range of reactant concentrations. The present process also has less potential for catalyst deactivation and undesirable by-product formation. This is particularly important in that it minimises olefin rich areas where by-product formation is likely to be highest.

c. It reduces costs because the addition of aliquots of cold monocarboxylic acid to the exit gases facilitates cooling of these gases between reactors. Use of the added reactant monocarboxylic acid to cool the incoming reactants to the second and subsequent reactors/stages may also eliminate the need to install relatively expensive heat exchangers and the maintenance costs associated therewith.

Any disadvantage arising from the increased used of the monocarboxylic acid in terms of cost is more than offset by the above advantages. The process of the present invention is particularly suited to making ethyl acetate from ethylene and acetic acid with optional recycle of any ethanol or diethyl ether formed.

The present invention is further illustrated with reference to the following Examples and Comparative Tests.

EXAMPLES

In the Examples STY is the Space Time Yield Measured in gEtAc/lcatalyst/hour

Catalyst Preparation:

Silica granules (Grace 57 grade, surface area 310 m$^2$/g, bulk density 0.4 g/ml, pore volume 1.03 ml/g, ca. 5–8 mm, 9.3 kg, ex W R Grace) were soaked in a solution of silicotungstic acid [$H_4SiW_{12}O_{40} \cdot 26H_2O$] (32 kg of 26% w/w aqueous solution) in order to impregnate the silica support with the silicotungstic acid catalyst. After this duration, excess catalyst solution was drained off. The resultant catalyst impregnated support pellets were then dried using a warm nitrogen stream to give a catalyst with a loading of 140 g/liter.

Catalyst Testing:

Three reactors, designed to simulate adiabatic operation, were set up in series with three vaporisers. The feedstream was heated in the first vaporiser and passed into the top of the first reactor at 175° C. and 1 Mpa pressure. The exit gases from the top reactor were then passed through the second vaporiser and fed into the second reactor at 176° C. The exist gases from this second reactor were then passed through the third vaporiser and into a third reactor at 176° C. Additional acetic acid was added into the vaporisers between the reactors. The exit gases from the third reactor were cooled and passed into a vapour-liquid separator at 20° C. The vapour stream from the separator was compressed and recycled to the first vaporiser. The liquid stream from the separator was reduced in pressure to atmospheric and samples were analysed by gas chromatography.

The feed to the first reactor was made up of fresh and recycled components made up of ethylene (3650 g/hr), acetic acid (652 g/hr), water (147 g/hr), ethanol (20 g/hr), diethyl ether (28 g/hr) and ethyl acetate (90 g/hr). The three reactors were each charged with 430 g of the silicotungstic acid catalyst specified above.

After the initial settling in period the catalyst activity was monitored by overall STY. Upon addition of acid via the second and third interbed vaporisers, the STY was increased to 236 gEtAc/lCat/h. for a period of 200 h.

Comparative Test (Not According to the Invention):

In a comparative test, the process of the above Example was repeated except that no additional acetic acid was fed to the second and third vaporiser stages. For a period of 100 h acetic acid was only supplied from the first vaporiser to the top reactor. Under these conditions the STY remained 226 gEtAc/lCat/h. The results of this and the Example are shown in the Table below:

|  | Acetic acid added to top reactor | Acetic acid added to second vaporiser | Acetic acid added to third vaporiser | ETAC STY (gEtAc/ lCat/h) |
|---|---|---|---|---|
| Example* | 652 | 110 | 110 | 236 |
| Comp. Test | 652 | 0 | 0 | 226 |

*According to the present invention.

Example 2

A simulation of a reactor used for the manufacture of ethyl acetate (EtAc) yielded the following data for the inlet to the adiabatic catalyst bed, the outlet to the catalyst bed and the reactor outlet after the addition of 5153 kg/hr acetic acid (AcOH) (at 25° C.) and 302 kg/hr water (at 40° C.). The molar ratio of ethylene to acetic acid was 12:1 at the inlet and was returned to 12:1 at the outlet to the reactor following reaction; this Example shows how this may be achieved whilst simultaneously lowering the temperature attained at the catalyst bed outlet. It should be noted that the reduction in temperature produced by the simulation is achieved by liquid injection alone and without making use of relatively expensive heat exchangers.

| Stream | Inlet to Catalyst Bed (kg/hr) | Outlet to Catalyst Bed (kg/hr) | After AcOH & water Injection (kg/hr) |
|---|---|---|---|
| Acetic Acid | 36355 | 30586 | 35738 |
| Ethylene | 202680 | 199967 | 199967 |
| EtAc | 7111 | 15576 | 15576 |
| Ether | 1404 | 1431 | 1431 |
| Water | 8196 | 8189 | 8492 |
| Ethanol | 1656 | 1656 | 1656 |
| Light Ends & Permanent Gases | 22440 | 22440 | 22440 |
| Heavy Ends | 6.3 | 6.3 | 6.3 |
| TOTAL | 279848 | 279851 | 285307 |
| Pressure (KPa (barg)) | 1200 (11) | 1200 (11) | 1200 (11) |
| Temperature (° C.) | 175.0 | 183.3 | 175.0 |
| Phase | Vapour | Vapour | Vapour |

Example 3

A simulation of a reactor used for the manufacture of ethyl acetate (EtAc) yielded the following data for the inlet to the adiabatic catalyst bed, the outlet to the catalyst bed and the reactor outlet after the addition of 5075 kg/hr acetic acid (AcOH) (at 25° C.). The molar ratio of ethylene to acetic acid was 12:1 at the inlet and 11.7:1 at the outlet to the reactor and thus this Example shows how this ratio may be maintained within the preferred range whilst simultaneously lowering the temperature attained at the catalyst bed outlet. It should be noted that the reduction in temperature produced by the simulation is achieved by liquid injection alone and without making use of relatively expensive heat exchangers.

| Stream | Inlet to Catalyst Bed (kg/hr) | Outlet to Catalyst Bed (kg/hr) | After AcOH Injection (kg/hr) |
|---|---|---|---|
| Acetic Acid | 30296 | 25488 | 30563 |
| Ethylene | 168900 | 166639 | 166639 |
| EtAc | 5926 | 12980 | 12980 |
| Ether | 1170 | 1193 | 1193 |
| Water | 6830 | 6825 | 6825 |
| Ethanol | 1380 | 1380 | 1380 |
| Light Ends & Permanent Gases | 18700 | 18700 | 18700 |
| Heavy Ends | 5.3 | 5.3 | 5.3 |
| TOTAL | 233207 | 233209 | 238285 |
| Pressure (KPa (barg)) | 1200 (11) | 1200 (11) | 1200 (11) |
| Temperature (° C.) | 175.0 | 183.3 | 175.0 |
| Phase | Vapour | Vapour | Vapour |

We claim:

1. A process for the production of a lower aliphatic ester, said process comprising reacting a lower olefin with a saturated lower aliphatic monocarboxylic acid in the vapor phase in the presence of a heteropolyacid catalyst wherein the reaction is carried out in a plurality of reactors set up in series such that gases exiting from a first reactor are fed as a feed gas to a second reactor and those exiting from the second reactor are fed as a feed gas to a third reactor and so on for the subsequent reactors, and wherein an aliquot of the reactant monocarboxylic acid is introduced as a liquid into the feed gas to the second and subsequent reactors so as to maintain the olefin to monocarboxylic acid ratio in the feed gas to each of the second and subsequent reactors within a range of 10:1 to 16:1.

2. A process according to claim 1 wherein the plurality of reactors are set up in series in such a way that each of the reactors is disposed in an axial mode with the feed and product gases traversing an axial path within each reactor from entering the top of the reactor until the product gases leave each reactor from the base thereof, the catalyst being positioned between the point of entry of the feed gas and the point of exit of the product gases.

3. A process according to claim 1 wherein the plurality of reactors is setup in a series of radial flow reactors whereby the feed gases enter at the top of a reactor, pass down the middle thereof and then outwards radially over the catalyst in said reactor.

4. A process according to claim 3 wherein each radial flow reactor in the series is of a tubular shape which in a planar view has the appearance of a set of three concentric tubes and wherein the feed gases enter from the top into the inner most tube and flow radially outward into a middle annular tube housing the catalyst bed and then, after the addition reaction has taken place over the catalyst bed to generate a gaseous stream of product gases comprising ethyl acetate and the unreacted catalyst bed flowing further radially into the outermost tube of said concentric tubular reactor to be fed as feed gas into a second such radial flow reactor and so on.

5. A process according to claim 3 wherein the reactant acid is introduced into the gaseous streams emergent from each of (a) the first reactor to maintain the desired reactant concentrations in said gaseous stream so as to enable said stream to be used as the feed gas for the second and (b) the second reactor which is fed as the feed gas to the third reactor and so on to each of the subsequent reactors along in the series.

6. A process according to claim 1 wherein the olefin reactant used is ethylene, propylene or mixtures thereof.

7. A process according to claim 1 wherein the saturated, lower aliphatic mono-carboxylic acid reactant is a C1–C4 carboxylic acid.

8. A process according to claim 1 wherein the mole ratio of olefin to the lower monocarboxylic acid in the reactant gases fed to the first reactor is in the range from 1:1 to 18:1.

9. A process according to claim 1 wherein the mole ratio of olefin to the lower monocarboxylic acid in the reactant gases fed to the first reactor is in the range from 10:1 to 14:1.

10. A process according to claim 1 wherein in the case of the manufacture of ethyl acetate from ethylene and acetic acid, the mole ratios of ethylene to acetic acid in the reactant gases fed to the first reactor is in the range from 1:1 to 18:1 and that of the feed gas to the second and subsequent reactors is maintained in the range from 10:1 to 16:1 by adding further aliquots of acetic acid to the feed gas to the second and subsequent reactors.

11. A process according to claim 1 wherein the process is carried out in one long reactor which has a plurality of catalyst beds set up in series and the acid is injected into the exit gases from the first bed to maintain the range of olefin to monocarboxylic acid within said range in the second and subsequent beds, said long reactor thereby comprises a plurality of individual reactors set up in series.

12. A process according to claim 1 wherein the process comprises at least four reactors set up in series.

13. A process according to claim 1 wherein the cooling between each of the reactors is achieved wholly or partially by the injection of the reactant acid, water or mixtures thereof into the feed gas to the second and subsequent reactors.

14. A process according to claim 1 wherein the heteropolyacid catalyst is silicotungstic acid used as a free acid or as a partial acid salt thereof supported on a siliceous support derived from a synthetic silica.

15. A process according to claim 14 wherein the supported heteropolyacid catalyst is suitably used as a fixed bed in each reactor.

16. A process according to claim 1 wherein the vapors of the reactant olefins and acids are passed over the catalyst at a GHSV in the range from 100 to 5000 per hour.

17. A process according to claim 1 wherein the addition reaction is carried out at a temperature in the range from 150–200° C. within which range the entry temperature of the reactant gases is from 160–180° C. and the temperature of the exit gases from each reactor is from 170–200° C.

18. A process according to claim 1 wherein the reaction pressure is at least 400 KPa depending upon the relative mole ratios of olefin to acid reactant and the amount of water used.

19. A process according to claim 2, wherein said catalyst is positioned midway between the point of entry of the feed gas and the point of exit of the product gases.

20. A process for the production of a lower aliphatic ester, said process comprising the steps of:
reacting, in a first reactor of a plurality of reactors set up in series, a lower olefin with a saturated lower aliphatic monocarboxylic acid in the vapor phase in the presence of a heteropolyacid catalyst;
feeding gases exiting from said first reactor as a feed gas to a second reactor;

feeding gases exiting from said second reactor as a feed gas to a third reactor, and so on for subsequent reactors; and introducing an aliquot of the reactant monocarboxylic acid as a liquid into the feed gas to the second and subsequent reactors so as to maintain the olefin to monocarboxylic acid ratio in the feed gas to each of the second and subsequent reactors within a range of 10:1 to 16:1.

21. A process according to claim 3, wherein a coolant comprising the reactant monocarboxylic acid is sprayed upwards into at least one of said radial flow reactors.

22. A process according to claim 21, wherein the coolant is sprayed around the center of the reactor.

23. A process according to claim 22, wherein the coolant is sprayed using one or more nozzles capable of delivering a fine spray of droplets having an average droplet dimension of less than 200 microns.

24. A process according to claim 23, wherein a plurality of said nozzles is employed, said plurality of nozzles being located below a catalyst bed of said reactor in grid form.

* * * * *